United States Patent
Varieur

(10) Patent No.: US 6,641,586 B2
(45) Date of Patent: Nov. 4, 2003

(54) CLOSURE SYSTEM FOR SPINAL FIXATION INSTRUMENTATION

(75) Inventor: Michael S. Varieur, Portsmouth, RI (US)

(73) Assignee: DePuy AcroMed, Inc., Raynham, MA (US)

( * ) Notice: Subject to any disclaimer, the term of this patent is extended or adjusted under 35 U.S.C. 154(b) by 45 days.

(21) Appl. No.: 10/062,305

(22) Filed: Feb. 1, 2002

(65) Prior Publication Data

US 2003/0149431 A1 Aug. 7, 2003

(51) Int. Cl.[7] ............................ A61B 17/56; F16B 23/00
(52) U.S. Cl. ............................. 606/61; 606/73; 411/403
(58) Field of Search ............................. 606/61, 72, 73; 174/65 SS; 411/427, 402, 403, 410

(56) References Cited

U.S. PATENT DOCUMENTS

| | | |
|---|---|---|
| 4,611,580 A | 9/1986 | Wu |
| 4,743,260 A | 5/1988 | Burton |
| 4,763,644 A | 8/1988 | Webb |
| 4,790,297 A | 12/1988 | Luque |
| 4,805,602 A | 2/1989 | Puno et al. |
| 4,887,596 A | 12/1989 | Sherman |
| 4,913,134 A | 4/1990 | Luque |
| 4,946,458 A | 8/1990 | Harms et al. |
| 4,950,269 A | 8/1990 | Gaines, Jr. |
| 5,005,562 A | 4/1991 | Cotrel |
| 5,129,388 A | 7/1992 | Vignaud et al. |
| 5,154,719 A | 10/1992 | Cotrel |
| 5,217,497 A | 6/1993 | Mehdian |
| 5,261,912 A | 11/1993 | Frigg |
| 5,261,913 A | 11/1993 | Marnay |
| 5,360,431 A | 11/1994 | Puno et al. |
| 5,375,956 A * | 12/1994 | Pennig ..................... 411/389 |
| 5,385,583 A | 1/1995 | Cotrel |
| 5,437,669 A | 8/1995 | Yuan et al. |
| 5,443,467 A | 8/1995 | Biedermann et al. |
| 5,474,555 A | 12/1995 | Puno et al. |
| 5,476,464 A | 12/1995 | Metz-Stavenhagen et al. |
| 5,520,689 A | 5/1996 | Schläpfer et al. |
| 5,536,268 A | 7/1996 | Griss |
| 5,545,165 A | 8/1996 | Biedermann et al. |
| 5,554,157 A | 9/1996 | Errico et al. |
| 5,667,508 A | 9/1997 | Errico et al. |
| 5,669,911 A | 9/1997 | Errico et al. |
| 5,672,176 A | 9/1997 | Biedermann et al. |
| 5,683,390 A | 11/1997 | Metz-Stavenhagen et al. |
| 5,690,630 A | 11/1997 | Errico et al. |

(List continued on next page.)

FOREIGN PATENT DOCUMENTS

| | | |
|---|---|---|
| DE | 3722 590 C1 | 12/1988 |
| FR | 2 624 720 | 6/1989 |
| GB | 2 173 104 A | 10/1986 |

*Primary Examiner*—Pedro Philogene
*Assistant Examiner*—David Bonderer
(74) *Attorney, Agent, or Firm*—Nutter, McClennen & Fish, LLP

(57) ABSTRACT

A closure system for fixing a spinal fixation element to a spinal fixation element receiving body includes a low profile outer locking nut for engaging an outer surface of the spinal fixation element receiving body and an inner set screw for engaging an inner surface of a spinal fixation element. The outer locking nut includes opposed proximal and distal ends, a generally cylindrical, low profile outer surface, an inner surface defining an inner bore, and a spinal fixation element closure surface provided on the distal end. An engagement element is formed on the inner surface adjacent the distal end for engaging an outer portion of the spinal fixation element receiving body so as to close the spinal fixation element to the spinal fixation element receiving body upon tightening of the engagement element. A driving element is formed at the proximal end within a periphery defined by the low profile outer surface and is configured to receive a driving tool to tighten the engagement element.

24 Claims, 3 Drawing Sheets

U.S. PATENT DOCUMENTS

| | | |
|---|---|---|
| 5,697,929 A | 12/1997 | Mellinger |
| 5,713,898 A | 2/1998 | Stücker et al. |
| 5,716,356 A | 2/1998 | Bidermann et al. |
| 5,725,527 A | 3/1998 | Biedermann et al. |
| 5,733,286 A | 3/1998 | Errico et al. |
| 5,738,685 A | 4/1998 | Halm et al. |
| 5,752,957 A | 5/1998 | Ralph et al. |
| 5,797,659 A * | 8/1998 | Fuller .................... 301/35.623 |
| 5,797,911 A | 8/1998 | Sherman et al. |
| 5,863,293 A | 1/1999 | Richelsoph |
| 5,879,350 A | 3/1999 | Sherman et al. |
| 5,882,350 A | 3/1999 | Ralph et al. |
| 5,910,142 A | 6/1999 | Tatar |
| 5,964,760 A | 10/1999 | Richelsoph |
| 5,989,254 A | 11/1999 | Katz |
| 6,443,953 B1 * | 9/2002 | Perra et al. .................... 606/61 |
| 6,520,963 B1 * | 2/2003 | McKinley .................... 606/61 |

* cited by examiner

CLOSURE SYSTEM FOR SPINAL FIXATION INSTRUMENTATION

FIELD OF THE INVENTION

The present invention relates to devices and systems for holding a spinal fixation element. More particularly, the invention provides closure systems including at least an outer locking nut having an inner nut driving configuration for attaching a spinal fixation rod to a vertebral coupling element such as a pedicle screw or a hook.

BACKGROUND OF THE INVENTION

The use of spinal fixation instrumentation to align and/or fix a desired relationship between adjacent vertebral bodies is well established. Such instrumentation typically includes a spinal fixation element, such as a relatively rigid fixation rod, that is coupled to adjacent vertebrae by attaching the element to pedicle screws which have been inserted into the patient's vertebrae or to spinal hooks which can be placed into a vertebral arch for coupling to the vertebral bodies. Once installed, the spinal fixation instrumentation holds the vertebrae in a desired spatial relationship, either until desired healing or spinal fusion has taken place, or for some longer period of time.

One example of a rod based spinal fixation system is provided in U.S. Pat. No. 5,005,562, issued Apr. 9, 1991 to Cotrel (which is hereby incorporated by reference). This system includes pedicle screws and spinal hook vertebral coupling elements (both screws and hooks) having integral U-shaped bodies that extend outward from the vertebrae to which they are attached. A spinal fixation rod is shaped as desired and fitted into the "U" of U-shaped bodies of adjacent vertebrae. The inner surfaces of the U-shaped body are threaded to accept a set screw, and rod is fixed to the vertebral coupling elements by threading a set screw into each of the U-shaped bodies to lock in the rod.

U.S. Pat. No. 5,545,165, issued Aug. 13, 1996 to Biedermann et al. (and incorporated herein by reference), illustrates an improvement in closure systems for fixing a rod to vertebral coupling elements over those provided by Cotrel. The Biedermann et al. system also uses pedicle screws and spinal hooks having U-shaped bodies that extend outward from the vertebrae to which they are attached. The U-shaped bodies of the Biedermann et al. system are threaded on both the inside and the outside. The rod is therefore locked in by both an inner set screw and an outer lock nut. In the illustrated embodiments, the inner set screw is adapted to be driven on its threads using a hex-shaped driver element, and the outer locking nut is provided with hex-shaped flat outer surfaces suitable for engagement with a wrench or similar driving tool.

U.S. Pat. No. 5,443,467, issued Aug. 22, 1995 to Biedermann et al. (and incorporated herein by reference) illustrates the use of an inner set screw and an outer lock nut to lock a rod into a U-shaped body in a polyaxial screw system. In this system, a pedicle screw having a spherical head is captured within a separate U-shaped receiver body. The angle of the screw with respect to the body can be changed until a head-locking element is tightened to lock the angle of the screw head within the receiver body. According to Biedermann et al., this combination of an inner set screw and an outer locking nut provides an advantage in that the force acting on the rod can be independently adjusted by either the inner set screw or the outer locking nut—a particularly useful advantage where the rod being fastened is curved and an exact fastening might only be possible by independent adjustment of the two closure elements. In addition, when tightened, the inner set screw and the outer locking nut tend to lock each other in their tightened positions.

While the closure systems of the Biedermann et al. patents have been quite successful, the illustrated embodiments necessarily involve the use of an externally engaging driving element such as a wrench. For many applications, this driving configuration poses no problems. In some applications, however, especially in lumbar spine applications where the curvature of the spine causes the U-shaped bodies to extend toward each other, the preferred placement of the spinal coupling elements may result in the U-shaped members being so proximate to each other that attachment of the outer locking nuts having external hex surfaces can be challenging for the surgeon.

SUMMARY OF THE INVENTION

The present invention provides closure devices and systems having smaller profiles that include internal driving elements to allow for spinal coupling elements to be placed closer to each other than had previously been possible. In a first aspect, the invention includes a low profile spinal fixation element closure device. The closure device includes opposed proximal and distal ends, a generally cylindrical, low profile outer surface, an inner surface defining an inner bore extending through the closure device, and a spinal fixation element closure surface provided on the distal end. An engagement element is formed on the inner surface adjacent the distal end for engaging a spinal fixation element receiving body so as to close the spinal fixation element to the spinal fixation element receiving body upon tightening of the engagement element. A driving element is formed at the proximal end within a periphery defined by the low profile outer surface and is configured to receive a driving tool to tighten the engagement element.

In a further aspect of the invention, a closure system for fixing a spinal fixation element to a spinal fixation element receiving body is provided having a low profile outer locking nut for engaging an outer surface of the spinal fixation element receiving body and an inner set screw for engaging an inner surface of a spinal fixation element. The outer locking nut includes opposed proximal and distal ends, a generally cylindrical, low profile outer surface, an inner surface defining an inner bore, and a spinal fixation element closure surface provided on the distal end. An engagement element is formed on the inner surface adjacent the distal end for engaging an outer portion of the spinal fixation element receiving body so as to close the spinal fixation element to the spinal fixation element receiving body upon tightening of the engagement element. A driving element is formed at the proximal end within a periphery defined by the low profile outer surface and is configured to receive a driving tool to tighten the engagement element.

The inner set screw includes a body having an outer surface, a proximal end and a distal end. A spinal fixation element closure surface is provided on the distal end, a fastening element is formed on the proximal end, and an engagement element is formed on the outer surface. The engagement element engages an inner portion of the spinal fixation element receiving body so as to close the spinal fixation element to the spinal fixation element receiving body upon tightening of the engagement element.

The outer locking nut and inner set screw are configured so that when the outer locking nut is engaged to an outer portion of the spinal fixation element receiving body and the inner set screw is engaged to an inner portion of the spinal fixation element receiving body, the fastening element of the inner set screw is accessible through the inner bore of the outer locking nut so that the outer locking nut and the inner set screw are independently tightenable with respect to the spinal fixation element receiving body.

A still further aspect of the invention provides a system for coupling a spinal fixation element to a patient's spine having a spinal fixation element receiving body, a low profile outer locking nut, and an inner set screw. The spinal fixation element receiving body includes a vertebral coupling element disposed on a first end of the body and a spinal fixation element receiving opening formed on a second end of the body. The body further includes an outer portion adapted to engage the outer locking nut and an inner portion adapted to receive and engage the inner set screw. The outer locking nut and inner set screw can be similar to those described above.

In specific embodiments of the invention, the engagement element of the outer locking nut can include threads formed on the inner surface adjacent to the distal end and the driving element of the outer locking nut can formed in the inner surface of the central bore, for example by including a female driving element including a plurality of angled sides. In addition, the inner bore of the outer locking nut can have a minimum diameter that is sufficiently large to permit a driving tool to extend into the bore to drive the inner set screw when the outer locking nut and the inner set screw are assembled to the spinal fixation element receiving body, and can further be sufficiently large to permit the inner set screw to pass through the inner bore of the outer locking nut.

An outer locking nut driving tool configured to engage the female driving element to drive and thereby tighten the outer locking nut to the spinal fixation element receiving body can be providing. This driving tool may also be hollow, defining an inner bore having an inner diameter sufficiently large to permit an inner set screw driving tool to pass through the outer lock nut driving tool so that the outer locking nut and the inner set screw can be tightened at the same time.

BRIEF DESCRIPTION OF THE DRAWINGS

The invention will be more fully understood from the following detailed description taken in conjunction with the accompanying drawings.

DETAILED DESCRIPTION OF THE INVENTION

Figure 1:
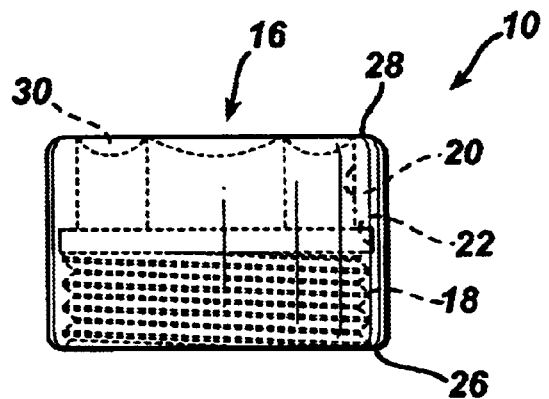
FIG. 1 a side view of an outer closure element of the invention with inner elements shown as ghosted.
Figure 2:
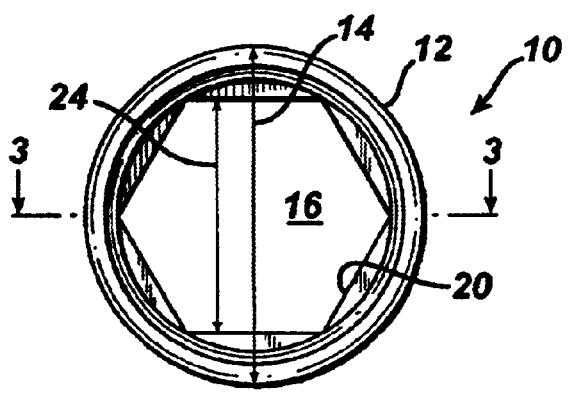
FIG. 2 is an end view of the outer closure element of FIG. 1.
Figure 3:
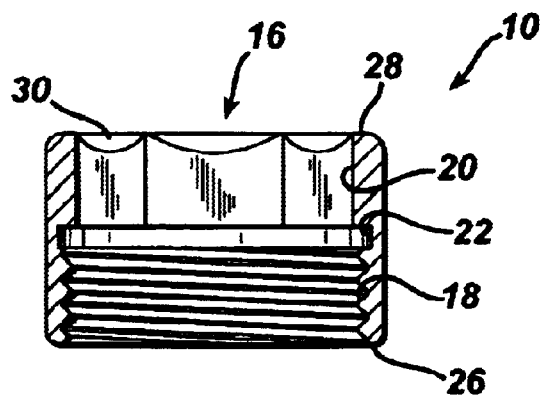
FIG. 3 is a cross-sectional view of the outer closure element of FIG. 2 taken along line 3—3.

The present invention provides closure devices and systems providing the benefits of known closure systems but also having smaller profiles and being drivable with tools having smaller profiles so that spinal coupling elements to be placed closer to each other than had previously been possible. As used herein, the terms "smaller profile" and "low profile" refer to a closure device or system having a smaller outer diameter than those conventionally used for similar applications, and not necessarily to a closure device or system having a lower height than conventional devices or systems. An outer locking nut 10 of the invention that may be used to fix a spinal fixation element (such as a spinal fixation rod) to a vertebral coupling element (such as polyaxial and monoaxial pedicle screws and spinal hooks) is illustrated in FIGS. 1 to 3.

The illustrated outer locking nut 10 has a smooth, generally cylindrical outer surface 12. Outer surface 12 contributes to the low profile of outer locking nut 10 as it lacks flat surfaces suitable for driving the outer locking nut using a wrench, resulting in a smaller overall nut diameter 14. Outer locking nut 10 defines a central bore 16 that can include a number of different bore regions including an inner threaded region 18 adjacent to its distal end 26 and an inner drive element 20, such as the illustrated female hex drive element, adjacent to its proximal end 28. In the illustrated embodiment, inner drive element 20 is formed in the inner surface of central bore 16, however, the inner drive element could also be formed in the proximal end 28 within the periphery defined by the outer surface 12 of outer locking nut 10. For example, blind bores could be formed in the proximal end 28 within the periphery defined by outer surface 12 so that outer locking nut 10 can be tightened or untightened using a spanner wrench.

Distal end 26 also provides a spinal fixation element closure surface which, when assembled to spinal fixation instrumentation, closes a spinal fixation element to a spinal fixation element receiving body. As the top or proximal end 28 of outer locking nut 10 is preferably rounded so as not to present sharp edges to tissue proximate to the nut when implanted. In addition, a counter sink, defining scallops 30 in the proximal end of the female hex drive element 20, can be provided to allow easy access to the female hex drive element. Central bore 16 can also include a thread relief region 22. Central bore 16 includes a minimum diameter 24 which also defines the largest diameter of parts or tools that might pass through the central bore.

In an exemplary embodiment useful for closing a spinal fixation rod to a vertebral coupling element, overall or outer nut diameter 14 can be about 14 millimeters and minimum diameter 24 can be about 10 millimeters. Similarly, the overall length of outer locking nut 10 can conveniently range from about 7 to about 9 millimeters while the inner threaded region 18 can extend about 4 millimeters along central bore 16 from its distal end 26 and thread relief region 22 can extend for about 1 millimeter beyond the threads. While threads are illustrated as an inner engagment element 18 for outer locking nut 10, a person of ordinary skill in the art will recognize that other suitable engaging elements, such as for example a tightenable pin and groove configuration, could serve to engage the outer locking nut to a spinal fixation element receiving body so as to tighten and hold a spinal fixation element therein.

Figure 4:
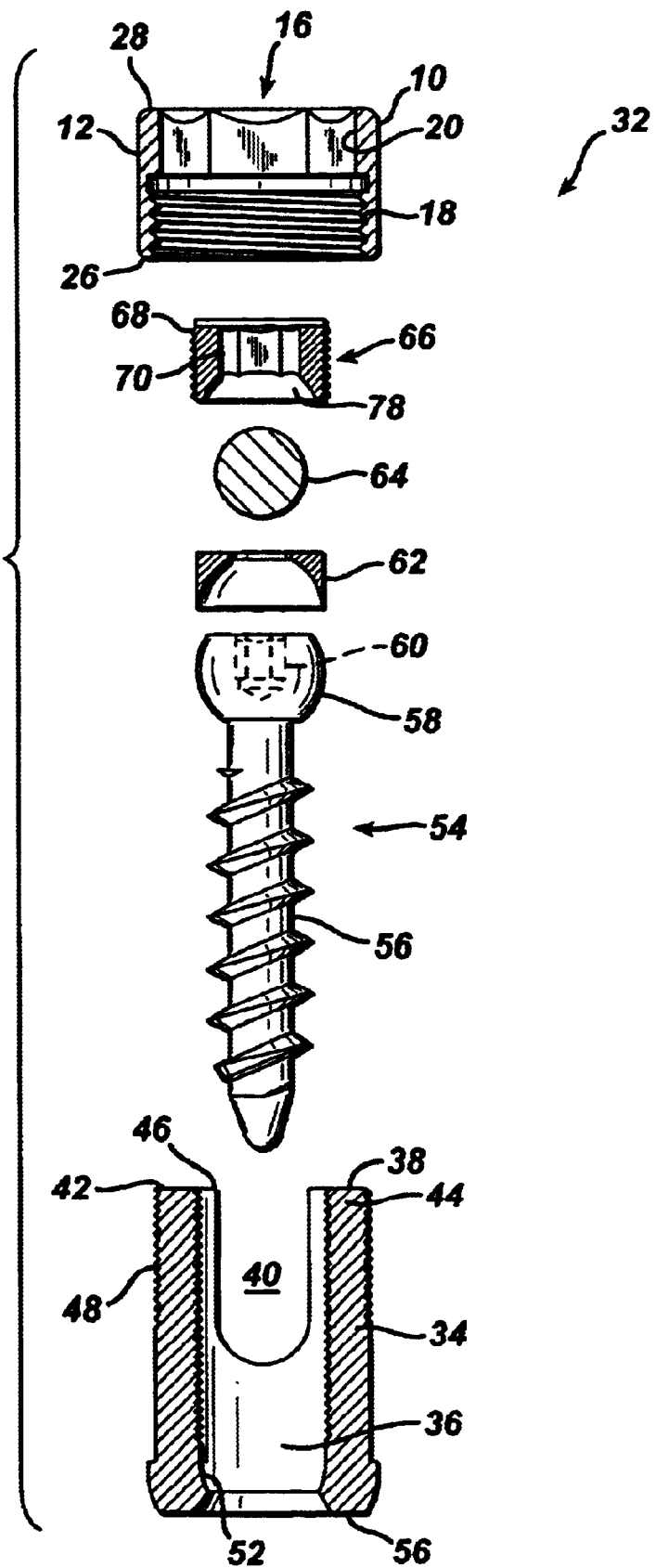
FIG. 4 is an exploded view of the outer closure element of FIG. 1 in use with a polyaxial pedicle screw vertebral coupling element system.
Figure 5:
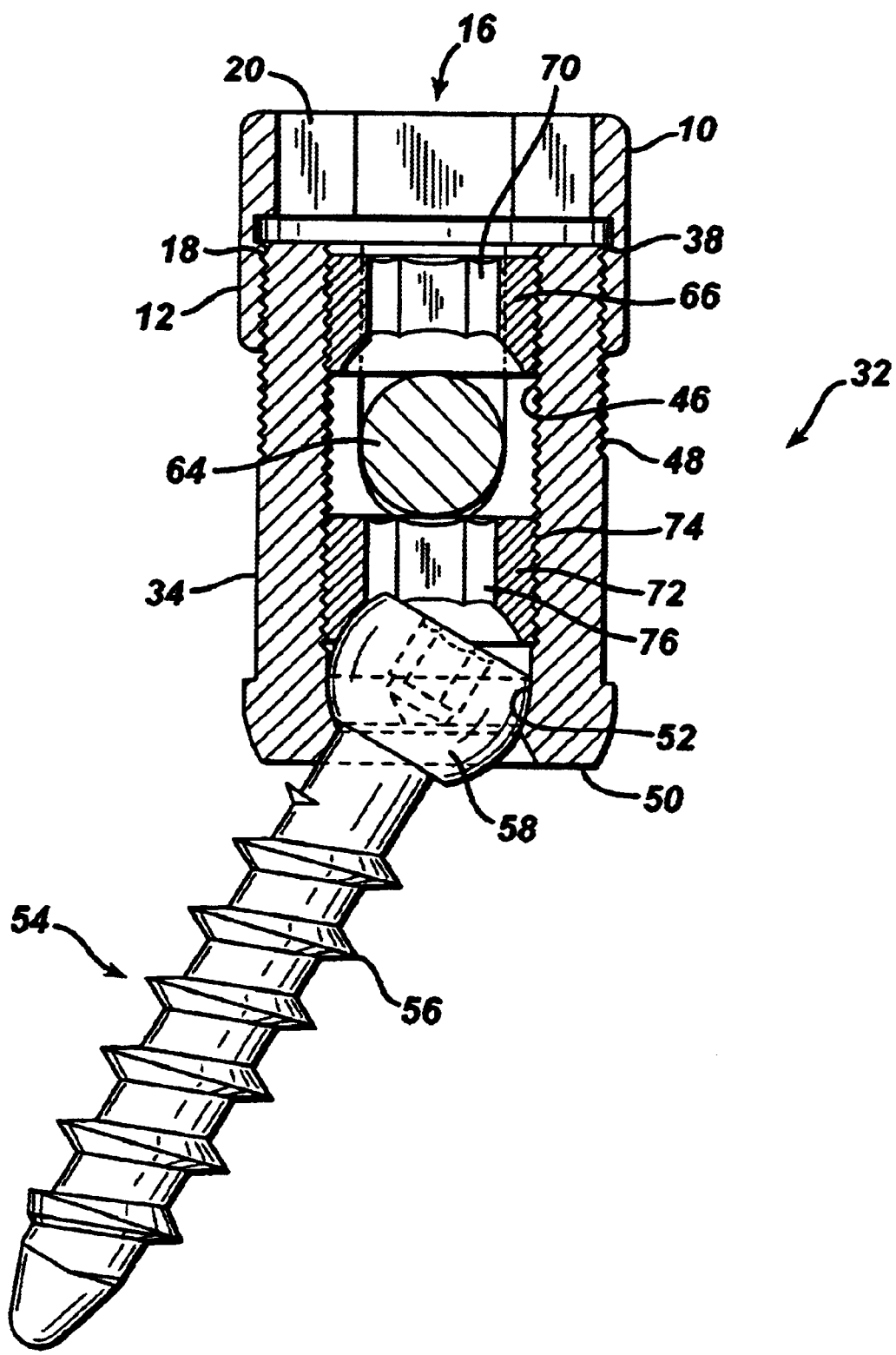
FIG. 5 is a side view with partial cross sectioning of the outer closure element of FIG. 1 in use with a polyaxial pedicle screw vertebral coupling element system.

Outer locking nut 10 is illustrated in FIG. 4 in an exploded cross-sectional view of a vertebral coupling system 32, and in an assembled vertebral coupling system in FIG. 5. Vertebral coupling system 32 includes a generally cylindrical receiver body 34 defining a central bore 36. The proximal end 38 of the receiver defines a rod receiving "U" shape 40 that defines the proximal end of the receiver into two legs 42, 44. Receiver body 34 also includes on its proximal end 38 inner 46 and outer 48 threads. At the distal end 50 of receiver 34, inner bore 36 includes a spherical region 52 configured to articulate with a spherical screw head. Vertebral coupling system 32 also includes pedicle screw 54 having a distal threaded shaft 56 for attachment to a vertebral body, a spherical head 58, and a proximal female hex element 60. Spherical head 58 is configured to articulate with spherical region 52 on assembly of the vertebral coupling system 32 while proximal female hex element 60 remains accessible from proximal end 38 of receiver body 34.

Head fixing element 62 (FIG. 4) is provided within central bore 36 of receiver body 34 to press spherical head 58 into locking contact with spherical region 52 upon tightening of the entire vertebral coupling system 32. Spinal fixation rod 64 fits within U-shaped opening 40 of receiver body 34 and presses on head fixing element 62 to lock the angle of pedicle screw 54 with respect to the receiver. In one alternative embodiment illustrated in FIG. 5, a threaded head fixing element 72 has external threads 74 and an inner female hex drive element 76 so that the threaded head fixing element can engage and be driven down inner threads 46 of receiver body 34 to lock the angle of pedicle screw 54 with respect to the receiver in advance of placing rod 64 within the U-shaped opening 40.

Referring again to both FIGS. 4 and 5, an inner set screw 66 having outer threads 68 and an inner female hex driver element 70 is engaged to inner threads 46 of receiver body 34 and driven distally to lock down rod 46 within U-shaped opening 40. A distal end 78 of inner set screw 66 forms a spinal fixation element closure surface which contacts rod 64 and closes the rod within U-shaped opening 40. While threads are illustrated as an outer engagment element 68 for inner set screw 66, a person of ordinary skill in the art will recognize that other suitable engaging elements, such as for example a tightenable pin and groove configuration, could serve to engage the outer locking nut to a spinal fixation element receiving body so as to tighten and hold a spinal fixation element therein.

Outer locking nut 10 is engaged to outer threads 48 of receiver body 34 to independently lock rod 64 into U-shaped opening 40. Preferably, minimum diameter 24 (FIG. 2) of central bore 16 of outer locking nut 10 is large enough to permit a driving tool to pass through the central bore in the outer locking nut to reach and operate female hex driver 70 (FIGS. 4 and 5) so that outer locking nut 10 and inner set screw 66 can be independently adjusted.

In one embodiment of the invention, minimum diameter 24 of central bore 16 of outer locking nut 10 is sufficiently large to permit inner set screw 66 to pass through the central bore. In this embodiment, outer locking nut 10 and inner set screw 66 can be engaged to vertebral coupling system 32 in any order and can be independently adjusted and, if necessary, independently removed. In a further embodiment of the invention, minimum diameter 24 of central bore 16 of outer locking nut 10 is sufficiently large to permit the use of a hollow outer nut driving element to engage and tighten the outer locking nut with the hollow driving element being large enough to permit an inner set screw 66 driving element to pass through the hollow outer nut driving element to engage and tighten the inner set screw. In this way, both outer locking nut 10 and inner set screw 66 could be adjusted simultaneously.

A person of ordinary skill in the art will appreciate further features and advantages of the invention based on the above-described embodiments. For example, the closure devices and systems of the invention can be used with a variety of vertebral coupling elements in addition to the polyaxial pedicle screw illustrated in FIGS. 4 and 5 above. By way of specific examples, the closure devices and systems of the invention could be used with vertebral coupling elements such as mono-axial pedicle screws (see, e.g., FIGS. 1 to 4 of U.S. Pat. No. 5,725,527 to Biedermann et al. which is incorporated herein by reference) or spinal hooks (see, e.g., FIG. 5 of Biedermann et al.). Accordingly, the invention is not to be limited by what has been particularly shown and described, except as indicated by the appended claims. All publications and references cited herein are expressly incorporated herein by reference in their entirety.

What is claimed is:

1. A low profile spinal fixation element closure device comprising:
    opposed proximal and distal ends;
    a generally cylindrical, low profile outer surface;
    an inner surface defining an inner bore extending through the closure device;
    a spinal fixation element closure surface provided on the distal end;
    an engagement element formed on the inner surface adjacent the distal end for engaging a spinal fixation element receiving body so as to close the spinal fixation element to the spinal fixation element receiving body upon tightening of the engagement element; and
    a driving element formed at the proximal end within a periphery defined by the low profile outer surface, the driving element configured to receive a driving tool to tighten the engagement element.

2. The device of claim 1, wherein the engagement element comprises threads formed on the inner surface adjacent to the distal end.

3. The device of claim 1, wherein the driving element is formed in the inner surface adjacent to the proximal end.

4. The device of claim 3, wherein the driving element comprises a female driving element including a plurality of angled sides.

5. The device of claim 3, in combination with a driving tool configured to engage the female driving element to drive and thereby tighten the closure device.

6. The device of claim 1, wherein the bore includes a minimum diameter sufficiently large to permit a driving tool to extend into the bore to drive an inner set screw disposed within the bore.

7. A closure system for fixing a spinal fixation element to a spinal fixation element receiving body comprising:
    a low profile outer locking nut for engaging an outer surface of the spinal fixation element receiving body having:
        opposed proximal and distal ends;
        a generally cylindrical, low profile outer surface;
        an inner surface defining an inner bore;
        a spinal fixation element closure surface provided on the distal end; and
        an engagement element formed on the inner surface adjacent the distal end for engaging an outer portion of the spinal fixation element receiving body so as to close the spinal fixation element to the spinal fixation element receiving body upon tightening of the engagement element; and
        a driving element formed at the proximal end within a periphery defined by the low profile outer surface, the driving element configured to receive a driving tool to tighten the engagement element; and
    an inner set screw for engaging an inner surface of a spinal fixation element having
        a body having an outer surface, a proximal end and a distal end;

a spinal fixation element closure surface provided on the distal end;

an engagement element formed on the outer surface for engaging an inner portion of the spinal fixation element receiving body so as to close the spinal fixation element to the spinal fixation element receiving body upon tightening of the engagement element; and a fastening element formed on the proximal end;

wherein when the outer locking nut is engaged to an outer portion of the spinal fixation element receiving body and the inner set screw is engaged to an inner portion of the spinal fixation element receiving body, the fastening element of the inner set screw is accessible through the inner bore of the outer locking nut so that the outer locking nut and the inner set screw are independently tightenable with respect to the spinal fixation element receiving body.

8. The system of claim 7, wherein the engagement element of the outer locking nut comprises threads formed on the inner surface adjacent to the distal end.

9. The system of claim 7, wherein the driving element of the outer locking nut is formed in the inner surface adjacent to the proximal end.

10. The system of claim 9, wherein the driving element of the outer locking nut comprises a female driving element including a plurality of angled sides.

11. The system of claim 7, wherein the inner bore of the outer locking nut includes a minimum diameter sufficiently large to permit a driving tool to extend into the bore to drive the inner set screw.

12. The system of claim 11, wherein the minimum diameter is sufficiently large to permit the inner set screw to pass through the inner bore.

13. The system of claim 9, further comprising an outer locking nut driving tool configured to engage the female driving element to drive and thereby tighten the closure device.

14. The system of claim 13, wherein the driving tool defines an inner bore having an inner diameter sufficiently large to permit an inner set screw driving tool to pass through the outer lock nut driving tool so that the outer locking nut and the inner set screw can be tightened at the same time.

15. A system for coupling a spinal fixation element to a patient's spine comprising:

a spinal fixation element receiving body having a vertebral coupling element disposed on a first end of the body and a spinal fixation element receiving opening formed on a second end of the body, the body including an outer portion adapted to engage an outer locking nut and an inner portion adapted to receive and engage an inner set screw;

a low profile outer locking nut for engaging an outer surface of the spinal fixation element receiving body having:

opposed proximal and distal ends;

a generally cylindrical, low profile outer surface;

an inner surface defining an inner bore;

a spinal fixation element closure surface provided on the distal end; and an engagement element formed on the inner surface adjacent the distal end for engaging the outer portion of the spinal fixation element receiving body so as to close the spinal fixation element to the spinal fixation element receiving body upon tightening of the engagement element; and a driving element formed at the proximal end within a periphery defined by the low profile outer surface, the driving element configured to receive a driving tool to tighten the engagement element; and an inner set screw for engaging an inner surface of a spinal fixation element having a body having an outer surface, a proximal end and a distal end;

a spinal fixation element closure surface provided on the distal end;

an engagement element formed on the outer surface for engaging the inner portion of the spinal fixation element receiving body so as to close the spinal fixation element to the spinal fixation element receiving body upon tightening of the engagement element; and a fastening element formed on the proximal end;

wherein when the outer locking nut is engaged to an outer portion of the spinal fixation element receiving body and the inner set screw is engaged to an inner portion of the spinal fixation element receiving body, the fastening element of the inner set screw is accessible through the inner bore of the outer locking nut so that the outer locking nut and the inner set screw are independently tightenable with respect to the spinal fixation element receiving body.

16. The system of claim 15, wherein the engagement element of the outer locking nut comprises threads formed on the inner surface adjacent to the distal end.

17. The system of claim 15, wherein the driving element of the outer locking nut is formed in the inner surface adjacent to the proximal end.

18. The system of claim 17, wherein the driving element of the outer locking nut comprises a female driving element including a plurality of angled sides.

19. The system of claim 17, further comprising an outer locking nut driving tool configured to engage the female driving element to drive and thereby tighten the outer locking nut to the spinal fixation element receiving body.

20. The system of claim 19, wherein the driving tool defines an inner bore having an inner diameter sufficiently large to permit an inner set screw driving tool to pass through the outer lock nut driving tool so that the outer locking nut and the inner set screw can be tightened at the same time.

21. The system of claim 15, wherein the inner bore of the outer locking nut includes a minimum diameter sufficiently large to permit a driving tool to extend into the bore to drive the inner set screw.

22. The system of claim 21, wherein the minimum diameter is sufficiently large to permit the inner set screw to pass through the inner bore.

23. The system of claim 15, wherein the vertebral coupling element is a pedicle screw.

24. The system of claim 15, wherein the vertebral coupling element is a spinal hook.

* * * * *